US006424694B1

(12) United States Patent
Molteni et al.

(10) Patent No.: US 6,424,694 B1
(45) Date of Patent: Jul. 23, 2002

(54) POSITIONING APPARATUS AND METHOD FOR TRANSVERSAL DENTAL X-RAY TOMOGRAPHY

(75) Inventors: Marcello Molteni; Gaetano Regalia, both of Milan (IT)

(73) Assignee: Dentsply Research & Development Corp.

( * ) Notice: Subject to any disclaimer, the term of this patent is extended or adjusted under 35 U.S.C. 154(b) by 0 days.

(21) Appl. No.: 09/679,765

(22) Filed: Oct. 5, 2000

Related U.S. Application Data

(60) Provisional application No. 60/158,705, filed on Oct. 8, 1999.

(51) Int. Cl.[7] .................................................. A61B 6/00
(52) U.S. Cl. .......................... 378/38; 378/205; 378/168
(58) Field of Search ........................... 378/38, 39, 168, 378/205, 207, 208, 209, 170

(56) References Cited

U.S. PATENT DOCUMENTS

| | | | |
|---|---|---|---|
| 3,936,641 A | * 2/1976 | Heimur | 250/439 |
| 4,012,638 A | 3/1977 | Altschuler et al. | 250/491 |
| 4,295,050 A | 10/1981 | Linden | 250/479 |
| 4,400,819 A | 8/1983 | Bens et al. | 378/20 |
| 4,409,616 A | 10/1983 | Ledley | 358/111 |
| 4,558,458 A | 12/1985 | Katsumata et al. | 378/20 |
| 4,741,007 A | 4/1988 | Virta et al. | 378/39 |
| 4,782,503 A | 11/1988 | Molitor et al. | 378/169 |
| 4,831,645 A | 5/1989 | Guenther et al. | 378/205 |
| 4,941,164 A | 7/1990 | Schuller et al. | 378/205 |
| 4,949,370 A | 8/1990 | Tanaka | 378/170 |
| 4,971,060 A | 11/1990 | Schneider et al. | 128/653.1 |
| 4,974,243 A | 11/1990 | McArdle et al. | 378/38 |
| 5,001,738 A | 3/1991 | Brooks | 378/170 |
| 5,044,009 A | 8/1991 | Klauser | 378/170 |
| 5,068,887 A | 11/1991 | Hughes | 378/170 |
| 5,090,047 A | 2/1992 | Angotti et al. | 378/170 |
| 5,113,424 A | 5/1992 | Burdea et al. | 378/170 |
| 5,219,288 A | 6/1993 | Kawamura et al. | 433/229 |
| 5,431,162 A | * 7/1995 | McArdle | 128/653.1 |
| 5,444,754 A | 8/1995 | Wederhorn et al. | 378/78 |
| 5,463,669 A | 10/1995 | Kaplan | 378/205 |
| 5,464,411 A | 11/1995 | Schulte et al. | 606/130 |
| 5,490,716 A | * 2/1996 | Naughton | 297/423.12 |
| 5,513,240 A | 4/1996 | Hausmann et al. | 378/170 |
| 5,629,972 A | 5/1997 | Hausmann et al. | 378/170 |
| 5,689,545 A | 11/1997 | Hopkins | 378/206 |
| 5,828,720 A | 10/1998 | Syrjanen | 378/78 |
| 5,828,721 A | 10/1998 | Schulze-Ganzlin et al. | 378/38 |
| 5,836,878 A | 11/1998 | Mock et al. | 600/415 |
| 5,921,927 A | 7/1999 | McArdle | 600/425 |

FOREIGN PATENT DOCUMENTS

| | | |
|---|---|---|
| EP | 365840 | 9/1994 |
| EP | 499595 | 11/1996 |
| EP | 904733 | 3/1999 |
| WO | 89/06828 | 7/1989 |

OTHER PUBLICATIONS

Dentsply Gendex, Orthoralix 9200; "The panoramic and cephalometric system with a wide range of advantages"; 15 pgs.

Superior Performance; "The Revolutionary Transversal Slicing System for Cross–Sectional Tomography"; 23 pgs; Revision 1, Jun. 1993.

* cited by examiner

*Primary Examiner*—Robert H. Kim
*Assistant Examiner*—Hoon K. Song
(74) *Attorney, Agent, or Firm*—Douglas R. Hura; James B. Bieber

(57) ABSTRACT

An apparatus and method used in dental transversal x-ray tomography provides off-line alignment of the patient denture impression with the bite block of a panoramic x-ray equipment, and allows accurate and reproducible patient positioning during the imaging process. An impression of the patient denture is taken on a special tray. The tray is mounted on the alignment apparatus and is aligned by using optical marking in correspondence with the target zone. The alignment apparatus is then mounted on a panoramic x-ray equipment, and the patient is invited to bite on the tray during the imaging process.

12 Claims, 12 Drawing Sheets

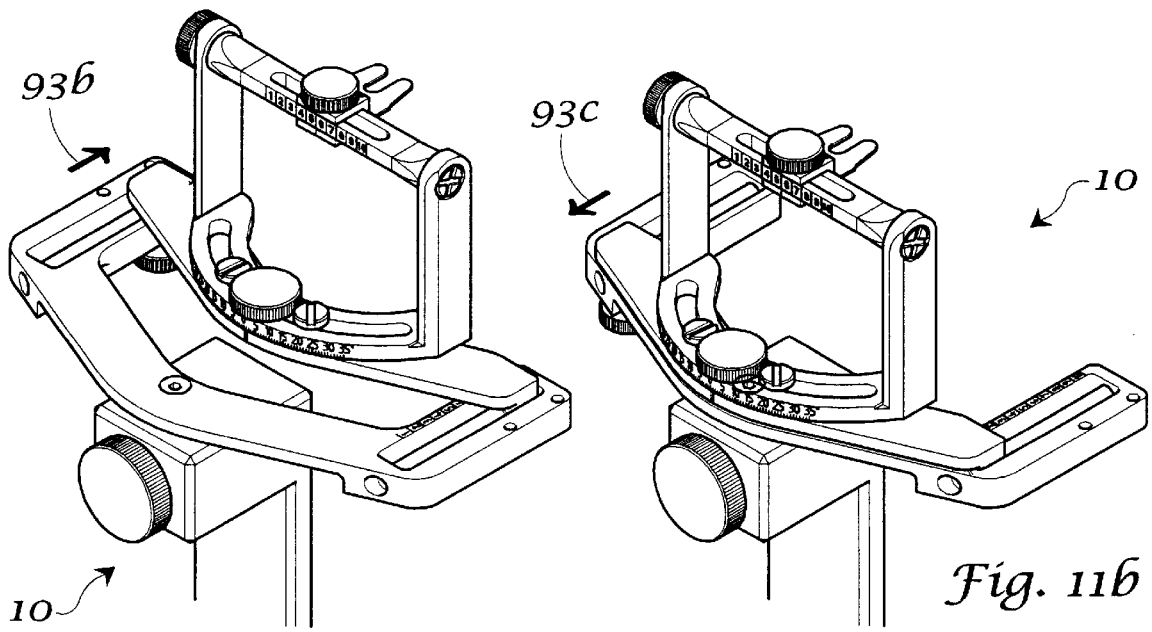
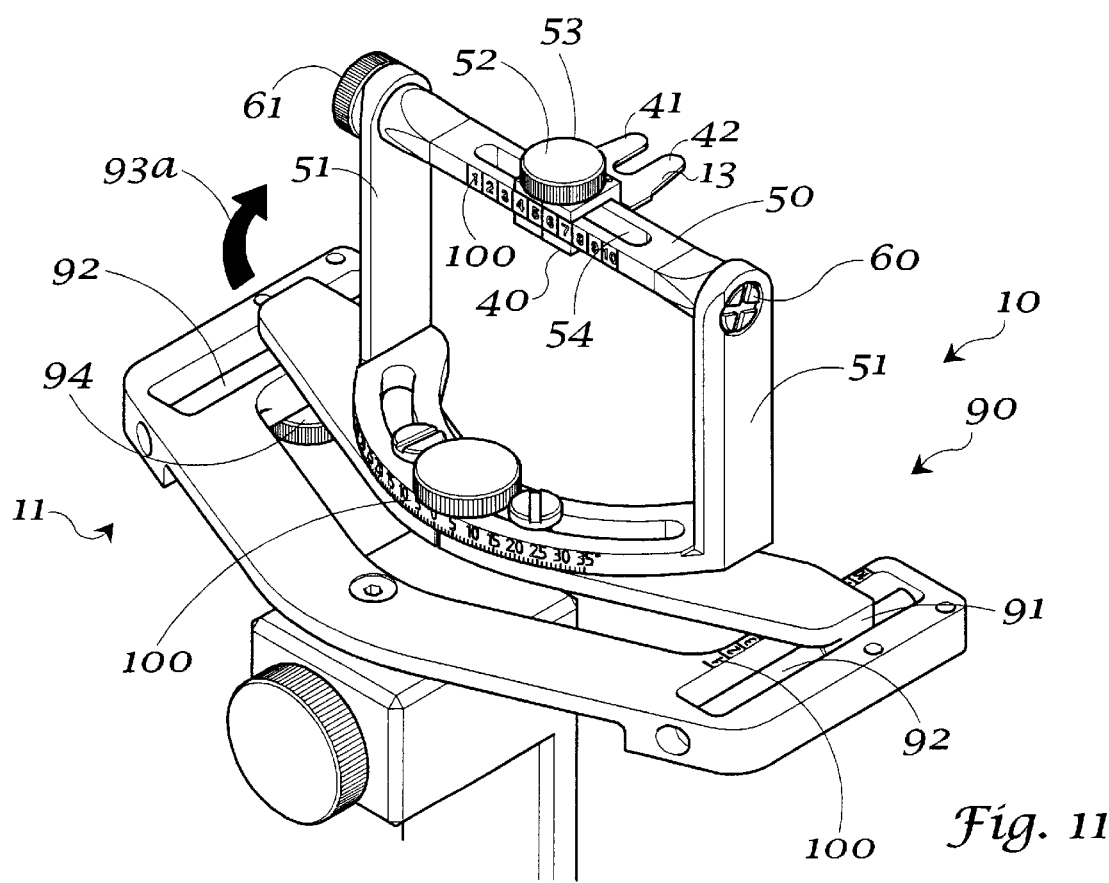

POSITIONING APPARATUS AND METHOD FOR TRANSVERSAL DENTAL X-RAY TOMOGRAPHY

This application claims priority from Provisional application Ser. No. 60/158,705, filed Oct. 8, 1999.

TECHNICAL FIELD

The present invention includes a positioning apparatus for use with transversal dental x-ray tomography. More particularly, the invention relates to a device which employs a dental impression held within an impression tray, and which aligns an x-ray shot by use of the impression.

BACKROUND OF THE INVENTION

Dental x-ray transversal tomography or scanography, is a projection modality provided by modern dental panoramic x-ray equipment for imaging the jaw in the transverse direction. Such images in the dental practice by using panoramic x-ray equipment is useful, especially in implantology, and compares with the tomographic imaging which can be obtained with much more complex and expensive tomographic equipment.

In combination with such imaging by using panoramic x-ray equipment, it is extremely important to provide an accurate and reproducible positioning of the patient. Transversal tomography equipment is capable of producing precise and accurate x-ray images. However, it has been found that it is often difficult to properly align the patient to take full advantage of the potential precision of the x-ray apparatus.

A method of aligning a patient is disclosed for example, in U.S. Pat. No. 5,444,754. The method includes imaging cross-sections on the same film as a respective longitudinal image of the dental arch. The cross-sectional images are exposed to include identifications for the sections. U.S. Pat. No. 5,431,162 employs a stent aligned with the imaging device so that a mark on the stent is aligned with a light beam. This patent also describes an exemplary x-ray machine, which disclosure is hereby incorporated by reference.

A need exists for an improved apparatus and method for properly aligning a patient when taking a transversal tomography x-ray image. The apparatus and method should naturally include ease of use and comfort to the patient.

SUMMARY OF THE INVENTION

It is therefore, an object of the invention to provide an apparatus and method for transversal dental x-ray tomography, allowing off-line alignment of the patient denture impression with respect to the biting point of a panoramic x-ray equipment, and accurate and reproducible patient positioning on-the-equipment during the imaging process.

The apparatus is a mechanical alignment device comprehending supports and joints, and is based on the following components and features:

A support tray, over which standard impression material is hardened to provide the reproduction of the patient denture at the occlusal plane.

The tray can either be a standard commercially available dental tray for impression, or a custom made tray for this application.

A positioner, holding the tray with denture impression, and fitting into the bite block holder of the panoramic x-ray equipment. The positioner is provided with slides and joints, allowing off-line free adjustments of the denture impression support: linear movement in the X and Y direction, rotation around X and Z axis.

A graduated scale in mm and degrees is provided for each adjustment movement. Transparent guide plates with silk screen reference of the target sections and teeth icons, allowing positioning of the region of interest with respect to the same target sections.

The first transparent plate is dedicated to the upper dentition, the second to the lower dentition.

A workbench support, provided with base, column and fastening screw, on which the positioner is mounted during the off-line adjustment phase.

The positioner is mounted upside for upper jaw and downside for lower jaw.

The method is articulated in several steps as follows:

(1) The patient bites the impression material to reproduce the denture occlusal plane (upper or lower jaw, using different denture support). A marker (steel ball or guttapercha cone) can be introduced into the impression, in correspondence with the region of interest.

(2) The positioner is placed on the workbench (upside for upper jaw, reversed for lower jaw), and the tray is mounted on the positioner.

(3) For upper jaw the tray is adjusted perfectly in the horizontal plane, for lower jaw a slight adjustment of the tray below the horizontal plane is allowed.

(4) The transparent guide plate is mounted on the positioner.

(5) The tooth icon is aligned with the diagnostic target zone on the impression, by using the vernier slides (X, Y axis) and the rotation around the Z axis.

(6) The tray position is fixed by securing the corresponding fastening screws.

(7) The panoramic x-ray equipment is prepared for transversal tomography.

(8) The positioner with the support tray is mounted on the bite point of the panoramic x-ray equipment.

(9) The patient is invited to bite into the impression to ensure a firm positioning, and then the imaging process is started.

The apparatus is designed to accommodate critical patient morphology, as derived by anatomical studies extended to patients of various race, age, and sex.

These and other objects of the invention, which will become apparent from the following description, are carried out by the invention as hereinafter described.

BRIEF DESCRIPTION OF THE DRAWINGS

FIG. 3 is a prospective view of an alternative icon guide;

FIGS. 8, 9, 10 and 11 are a series of photographs showing the relative freedom of movement obtainable with the positioning apparatus of FIG. 1.

PREFERRED EMBODIMENTS FOR CARRYING OUT THE INVENTION

Figure 7:
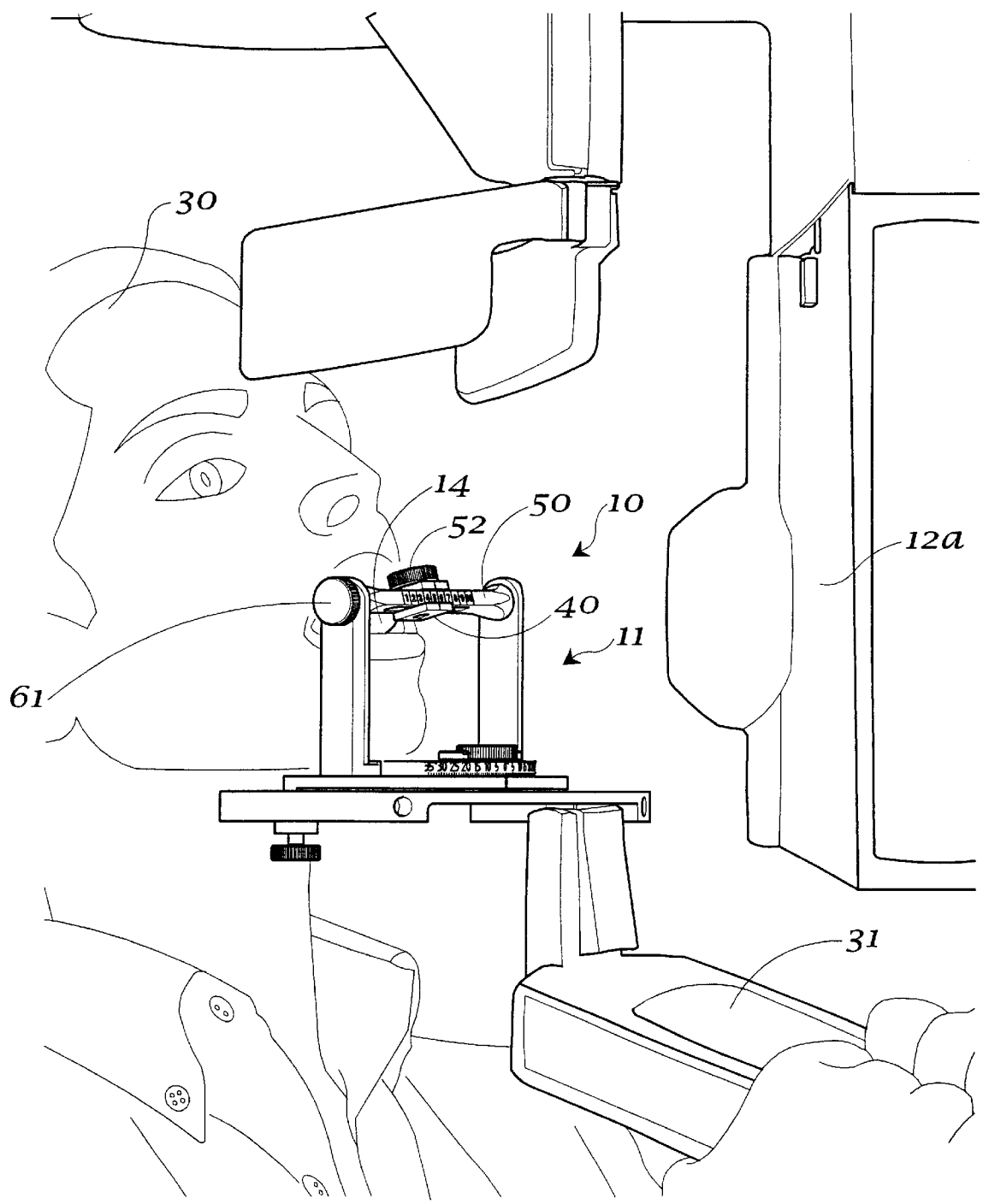
FIG. 7 is a perspective view of the combination shown in FIG. 4, shown being employed with a patient.

A positioning apparatus according to the concepts of the present invention is shown by way of example in the drawings by the number 10. Positioning apparatus 10 includes a universally adjustable holder 11 that can be selectively positioned upon a workbench support 12 or a dental x-ray machine 12a (FIG. 7). Holder 11 is provided with an attaching element 13 for affixing a standard dental impression tray 14 thereto. By "universally adjustable" it is understood that holder 11 is provided with multiple adjusting mechanisms (to be more fully described below) that allow the affixed impression tray 14 to be moved in at least one of and preferably all of an x, y and z coordinate direction.

Positioning apparatus 10 is also provided with a removable transparent icon guide 20. Icons 21 are provided upon guide 20, such that when guide 20 is affixed to positioning device 10, at least one icon 21 is positioned generally in a spaced opposing relation to impression tray 14 also affixed to positioning device 10.

Figure 5:
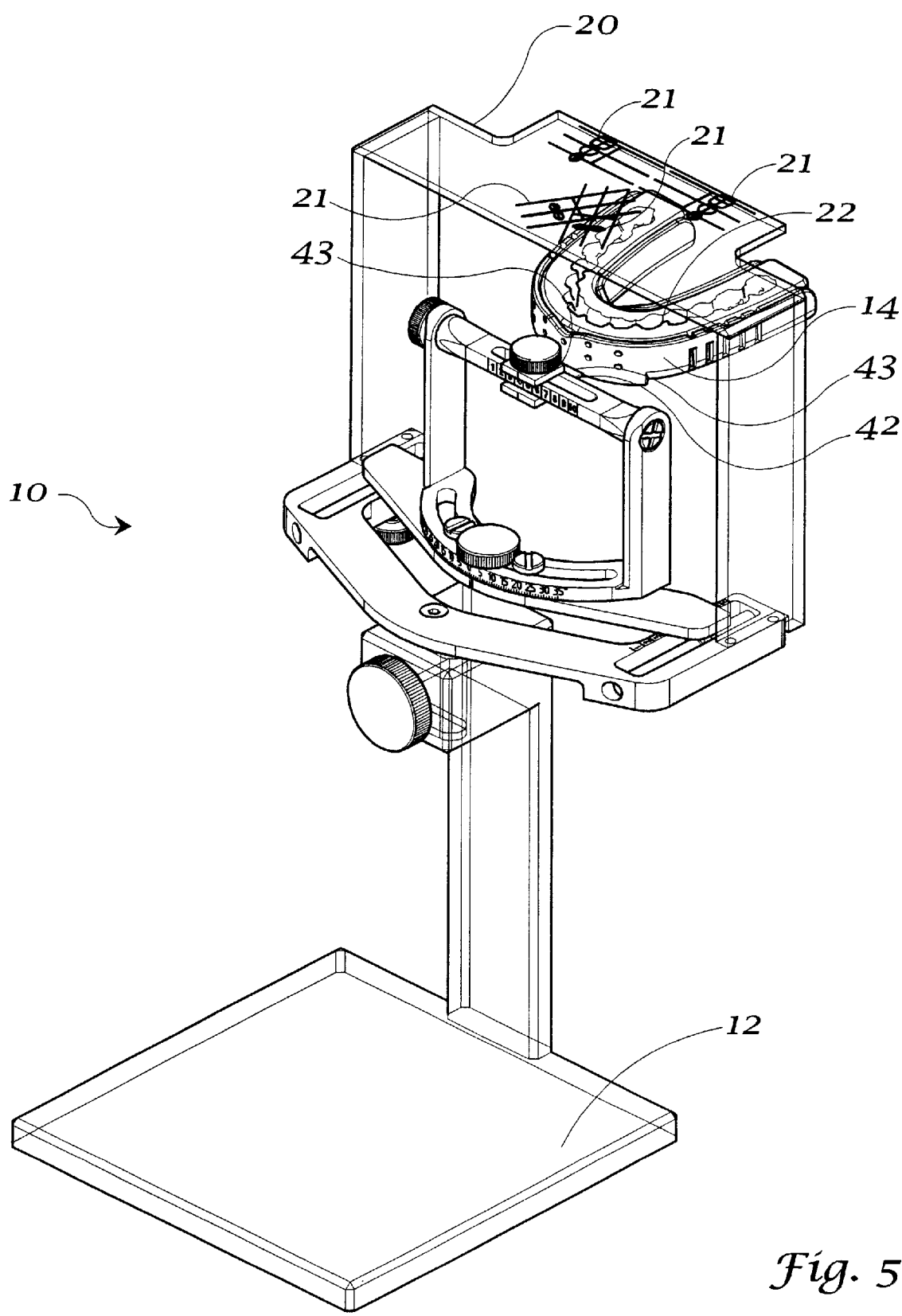
FIG. 5 is a photograph showing a dental impression formed within impression material in a dental impression tray, and the tray is positioned upon the positioning apparatus of FIG. 1.

The user employs impression tray 14 to prepare an impression of a dental arch or a desired portion of a dental arch in a conventional manner. The taking of dental impressions is well known and need not be described here. The impression material, shown by number 22 in FIG. 5, is allowed to at least partially set. Impression tray 14 is then affixed to positioning device 10 (in a manner to be described below) and icon guide is affixed to positioning device 10 in the spaced, opposing relation previously described. By universally adjusting the position of impression tray 14, an icon 21 can be caused to be in a specific position relative to impression tray 14 and hence to a specific and selected part of the dental arch. The adjusting mechanism is then locked into that position and the icon guide 20 is removed. The positioning apparatus 10 is then affixed to the x-ray machine 12a and the patient is invited to bite onto the dental impression 22 still held within impression tray 14 (FIG. 5).

In this manner, the resulting x-ray image will be taken at the precise location indicated by the positioning of icon 21 during the set-up described hereinabove. The resulting x-ray image is precisely aligned.

Figure 1:
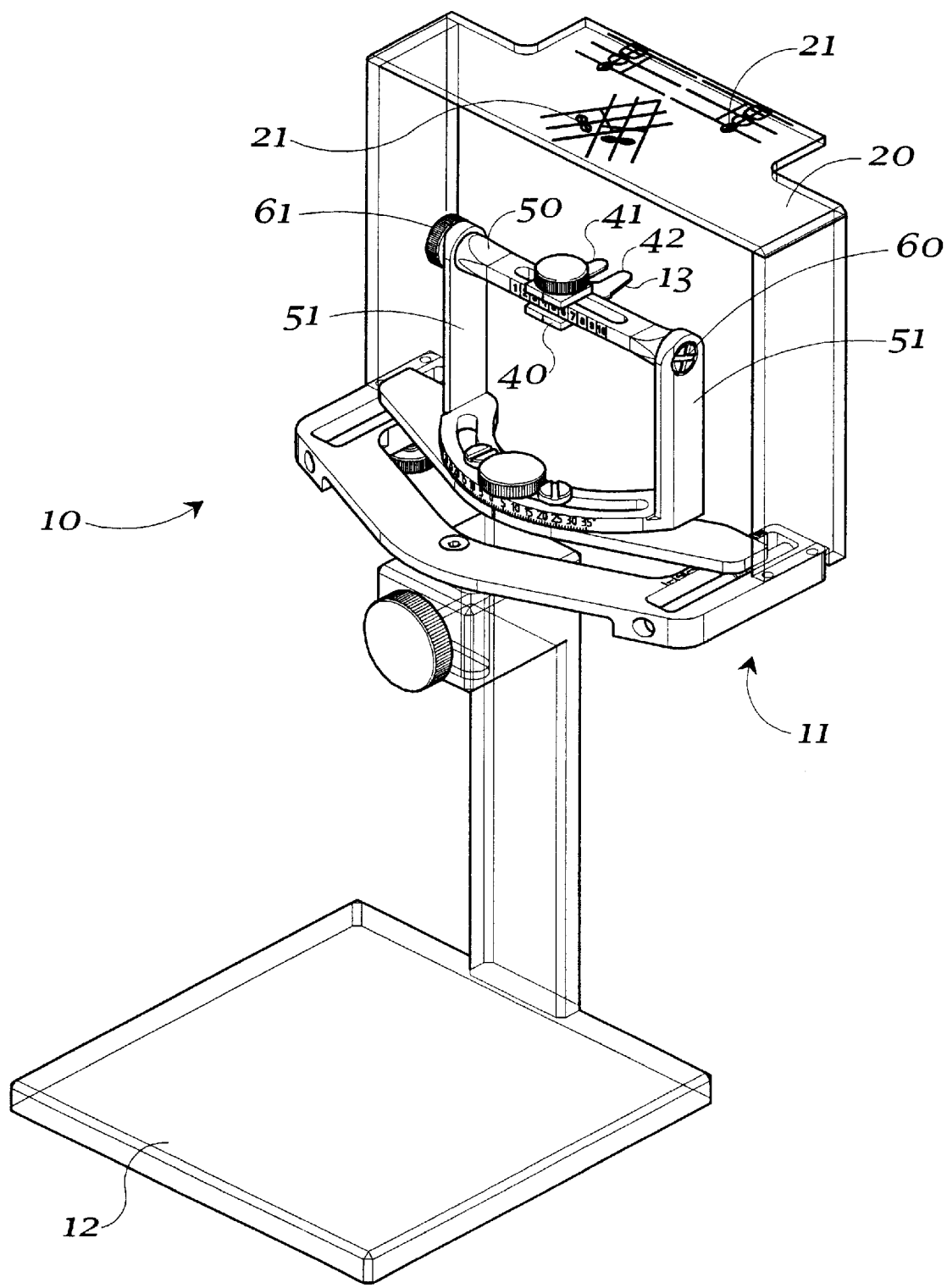
FIG. 1 shows the positioning apparatus of the present invention secured within a workbench support.
Figure 2:
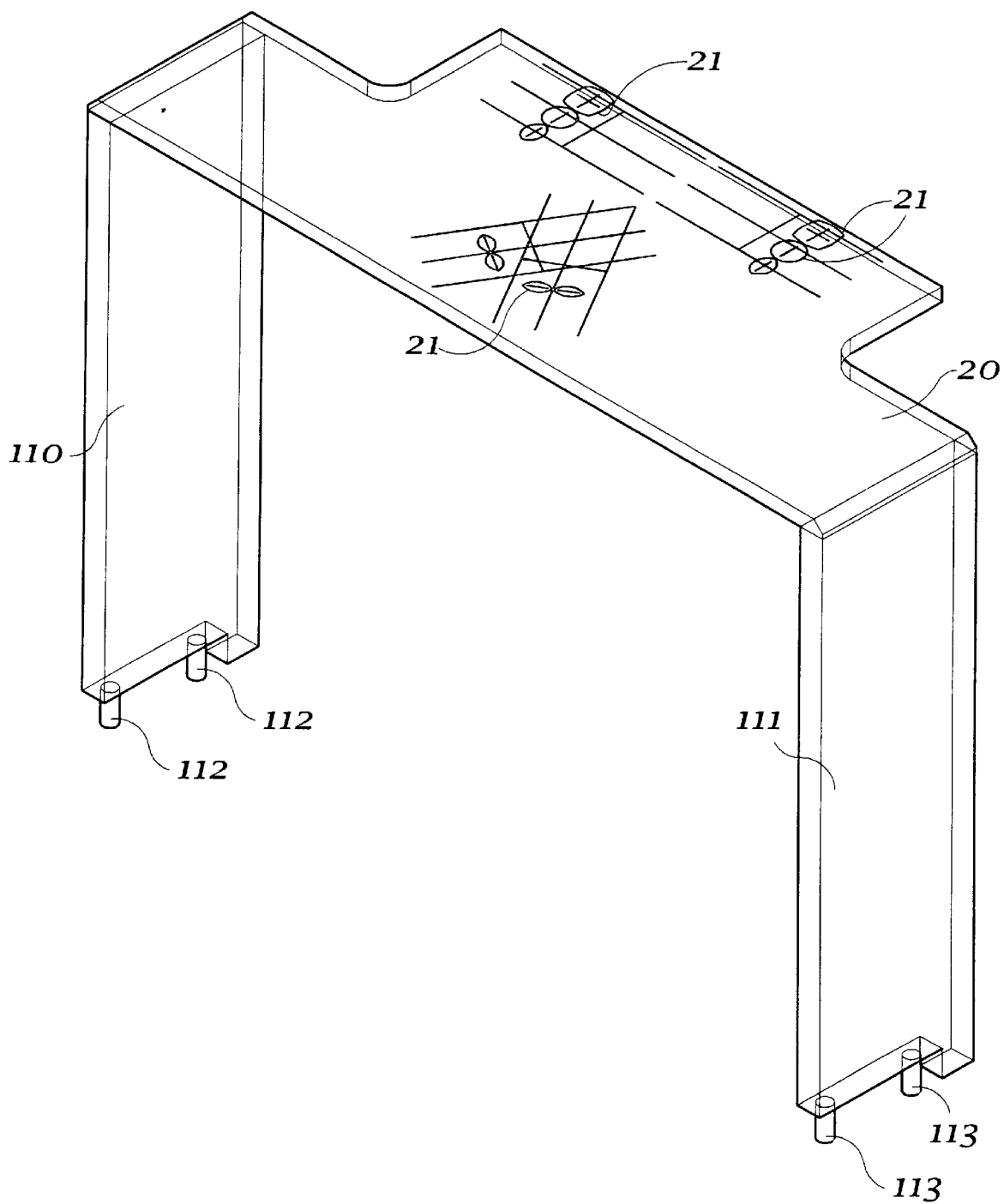
FIG. 2 shows a perspective close-up view of a transparent icon guide of FIG. 1.

FIG. 1 shows positioning device 10 in place upon workbench support 12, where the steps of aligning impression tray 14 with respect to an icon 21 carried by icon guide 20 can be accomplished. A second icon guide 24 is shown in FIG. 2. Icon guides 20 and 24 may be alternatively useful for example in taking adult x-ray images, pediatric images, anterior or posterior shots, partial images, or the like. It will be understood that any such icon guide is within the scope of the invention.

Figure 5A:
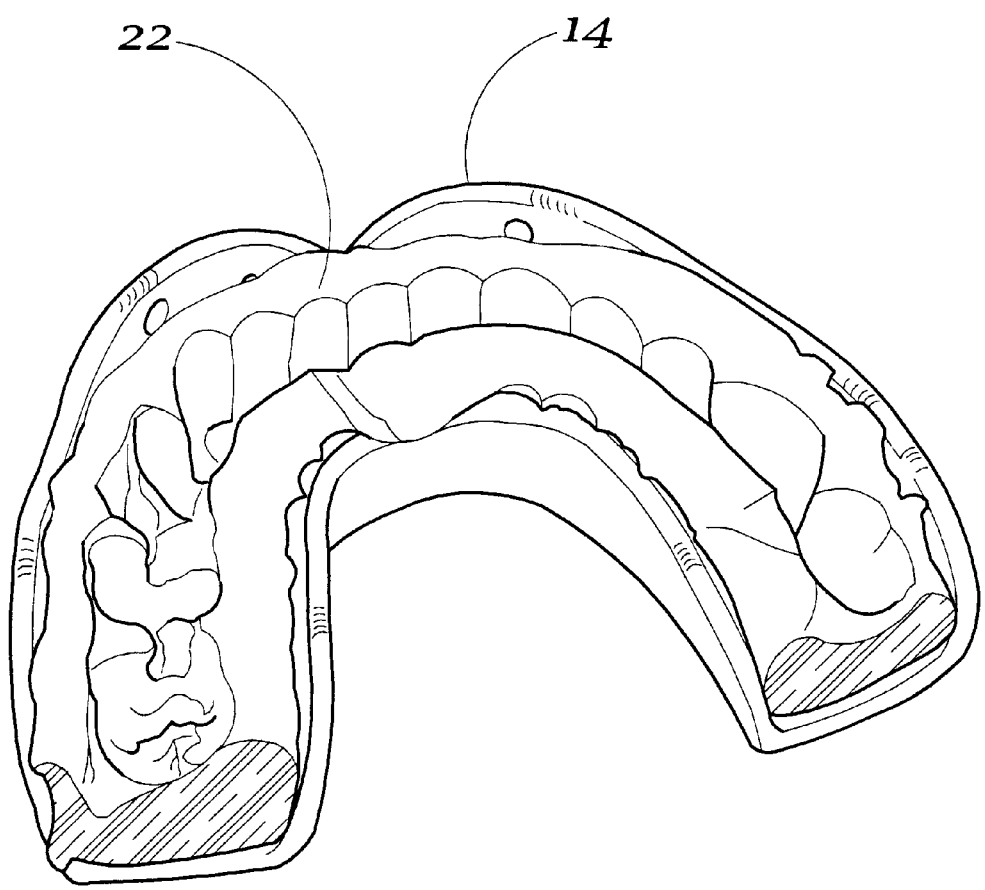
FIG. 5a is a close up view of the impression tray of FIG. 5.
Figure 6:
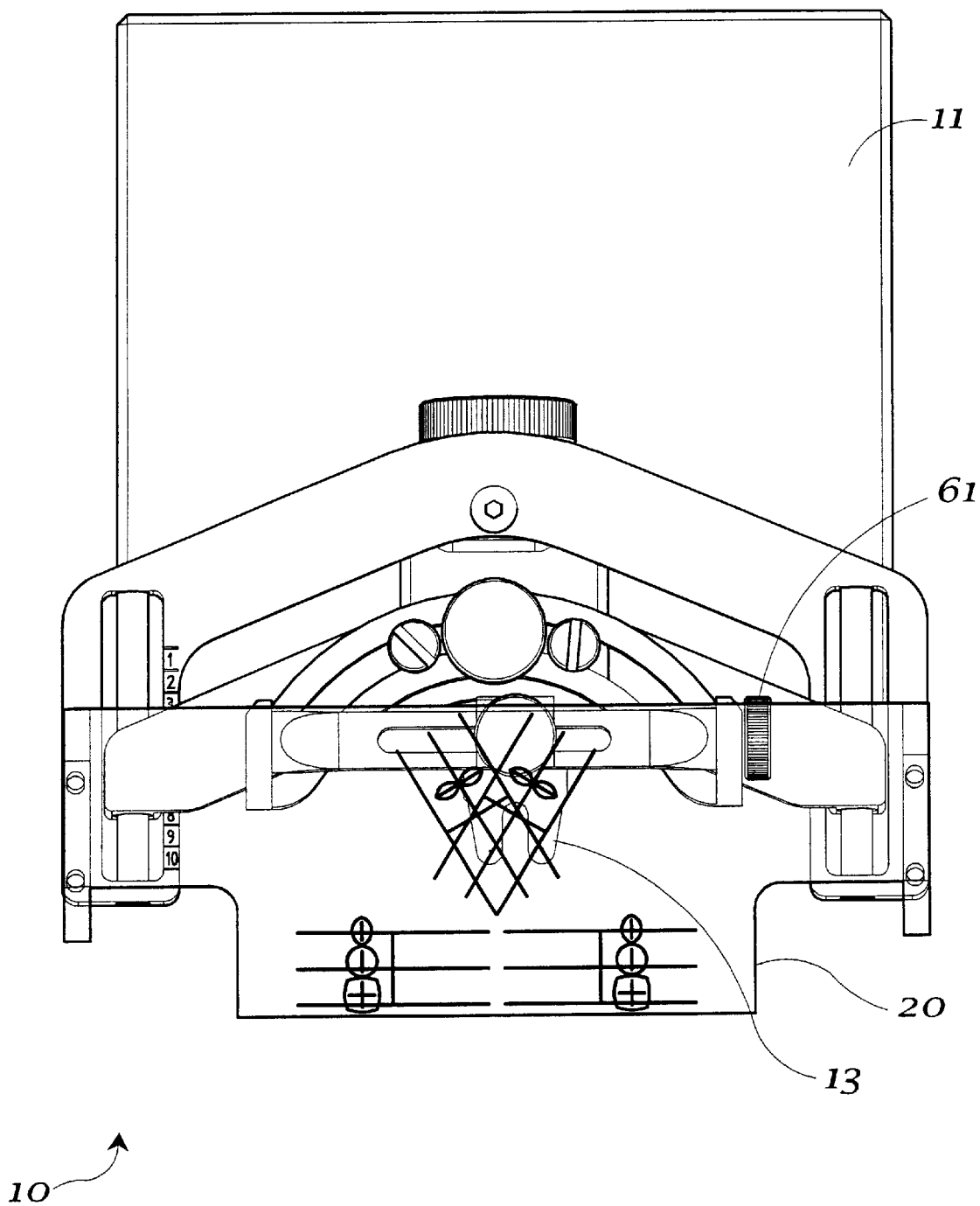
FIG. 6 is a top, plan view of the apparatus of FIG. 1.

FIG. 5a shows a substantially standard dental impression tray. Such trays and their use are well known in the art. The only requirement for an impression tray being useful in combination with the present invention is that there must be some means to affix, and more preferably, removably affix impression tray 14 to positioning device 10, which will be discussed more fully hereinbelow.

FIG. 5 shows positioning device 10 in place upon workbench support 12 and with means to affix an impression tray 14. Further, a formed impression 22 is held within impression tray 14. Further still, transparent icon guide 20 is affixed to positioning apparatus 10 in the aforesaid spaced, opposing relation to impression tray 14. Icons 21 re carried by icon guide 20, and because icon guide 20 is transparent, a user can see through icon guide 20, such that as impression tray 14 is adjustably positioned, the user can see through icon guide 20 and adjust the position of impression tray 14 so that a specific portion of impression 22 is directly opposed with an icon 21. Icon 21 may be thought of as being a "crosshairs" in regard to function, although there is no intention to indicate a specific shape of icon 21. Icon 21 can be a dot, a line, a circle, an oval, a square, a triangle, a trapezoid, a letter, a number, any regular or irregular shape, a representation of a tooth or teeth or other dentition, a series of any such articles, or any other indicia that may be desired or useful. Icon 21 may be painted, silk-screened or otherwise placed upon guide 20 or 24 as shown in the drawings. Although not shown, icon 21 could also be a decal, an etching or some other physical structure such as a hole, a post, a pin, or the like, or a combination of any of these mentioned.

FIG. 7 shows the positioning apparatus 10 of the present invention in place upon an x-ray machine 12a and wherein a patient 30 is biting upon the impression 22 held within impression tray 14. While the present invention has particular application to dental x-ray transversal tomography, and as such can be used with such an x-ray machine, it also has application to any dental or even other medical x-ray machines or stand. Therefore, any conventional x-ray machine is within the scope of the present invention. It is merely required to provide a means of affixing apparatus 10 to the x-ray machine 12a, such as by using a conventional hand-held 31 configured to be affixable to apparatus 10, or any other conventional method.

FIGS. 8–11 show the range of movement facilitated by positioning apparatus 10. Positioning apparatus 10 is shown in FIG. 1, removably affixed to workbench support 12. Positioning apparatus 10 in FIGS. 8–11 does not have an icon guide 20 or an impression tray 14 in place, so that the range of adjustable movement of positioning device 10 can be more clearly seen. However, there is shown one means of mounting impression tray 14 to positioning apparatus 10. This includes support bar 40 which is removably affixable to impression tray 14. In the embodiment of the invention shown in the drawings, bar 40 includes first and second prongs 41 and 42, respectively. Prongs 41 and 42 can be inserted into a slot 43 (FIG. 5) to hold and support impression tray 14.

For the sake of this discussion with respect to FIGS. 8–11, the range of adjustable motion of positioning apparatus 10 will be described with respect to support bar 40. It is understood that when an impression tray 14 is affixed to positioning apparatus 10, such as by use of support bar 40, the impression tray 14 will likewise be adjustable as to its position. With this in mind, FIGS. 11, 11a and 11b show a reciprocal, horizontal motion achievable with the adjusting devices of the positioning apparatus 10.

Figure 8A:
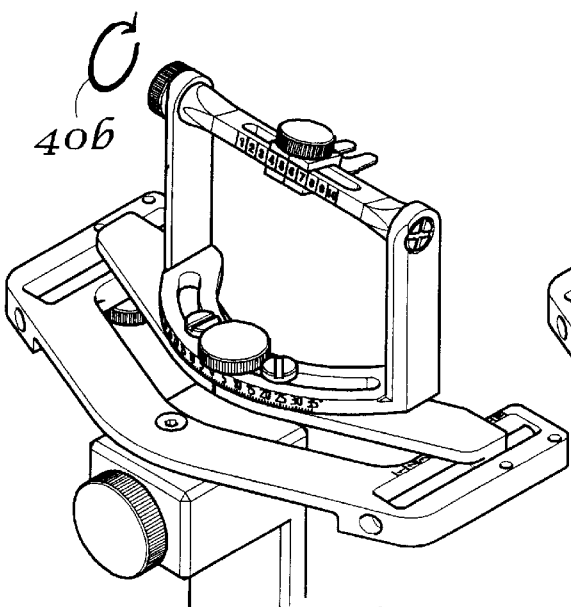
Figure 8B:
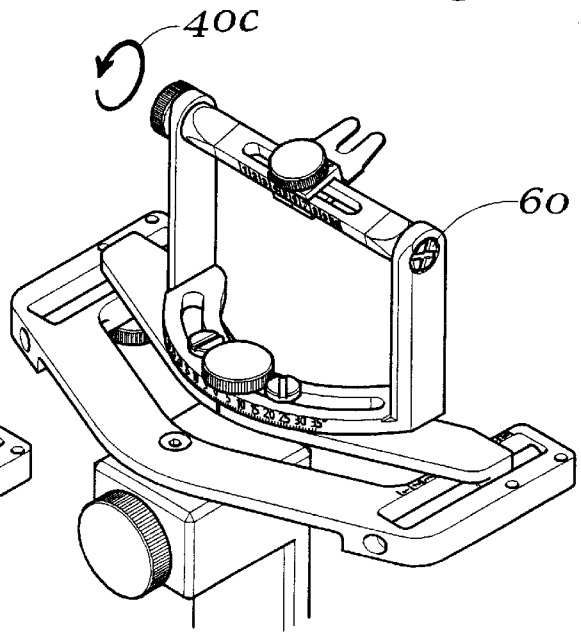
Figure 8:
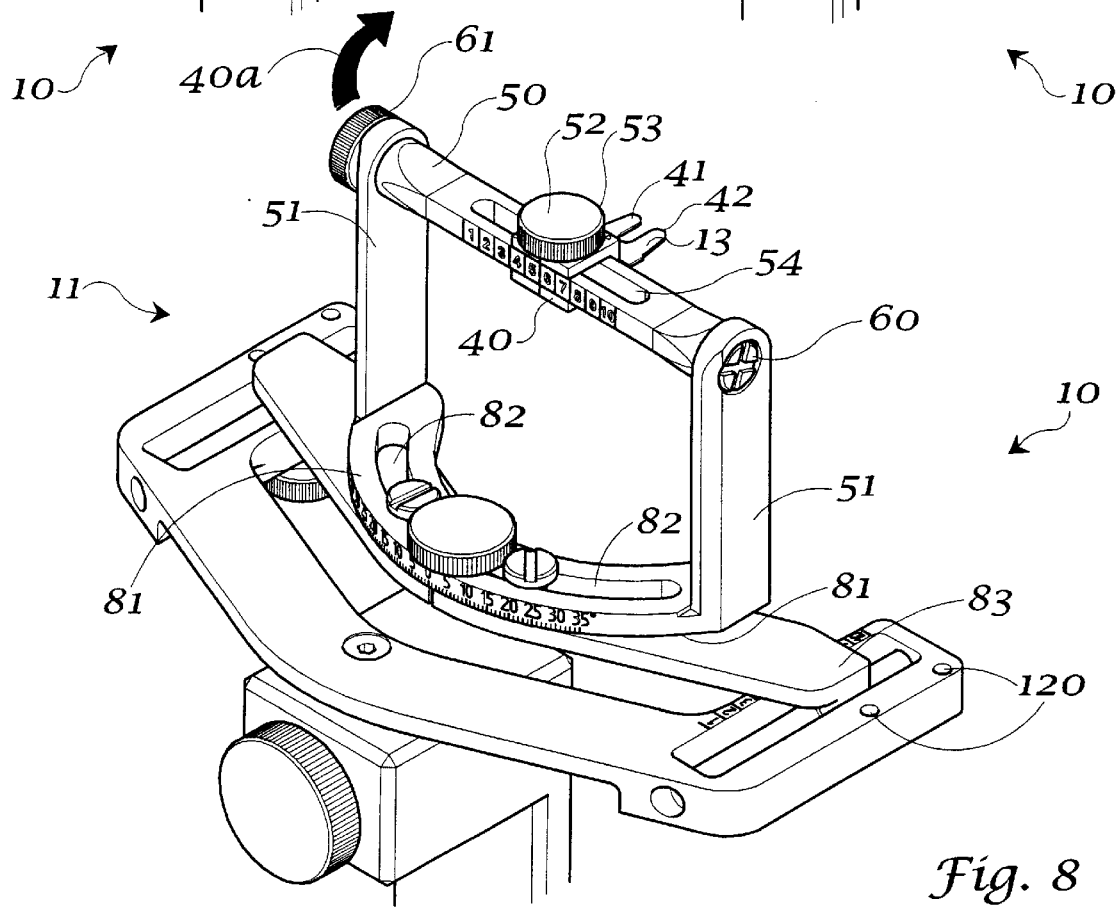

FIG. 8 shows an articulate adjustable position and shows that the support bar 40 can be adjustable from an upright position to a position 180° therefrom, or any position therebetween.

Figure 9A:
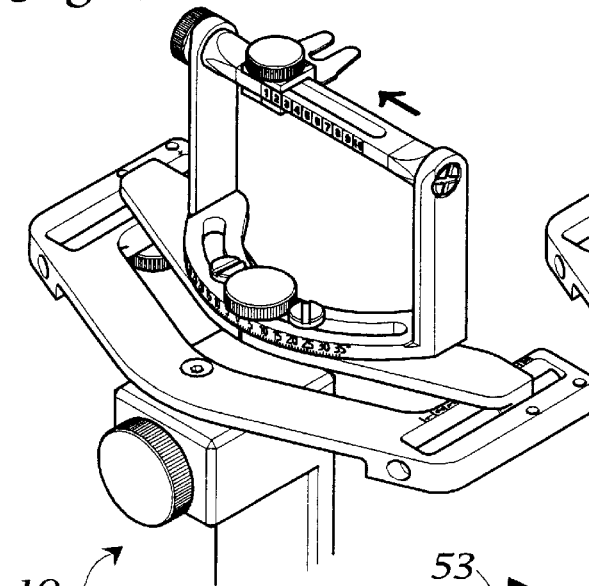
Figure 9B:
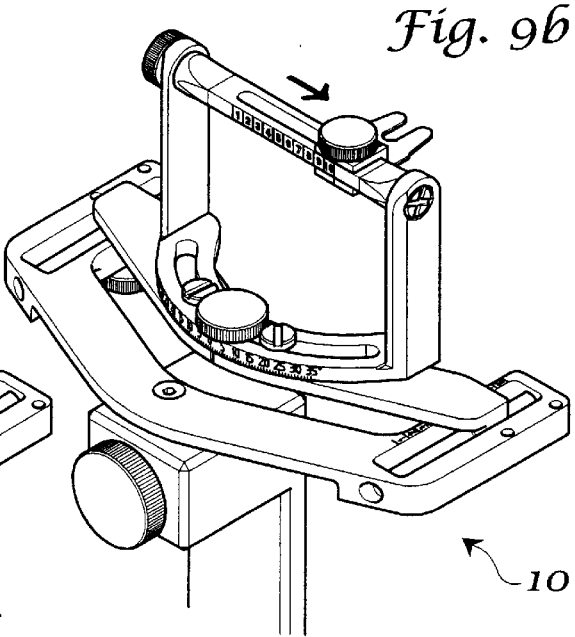
Figure 9:
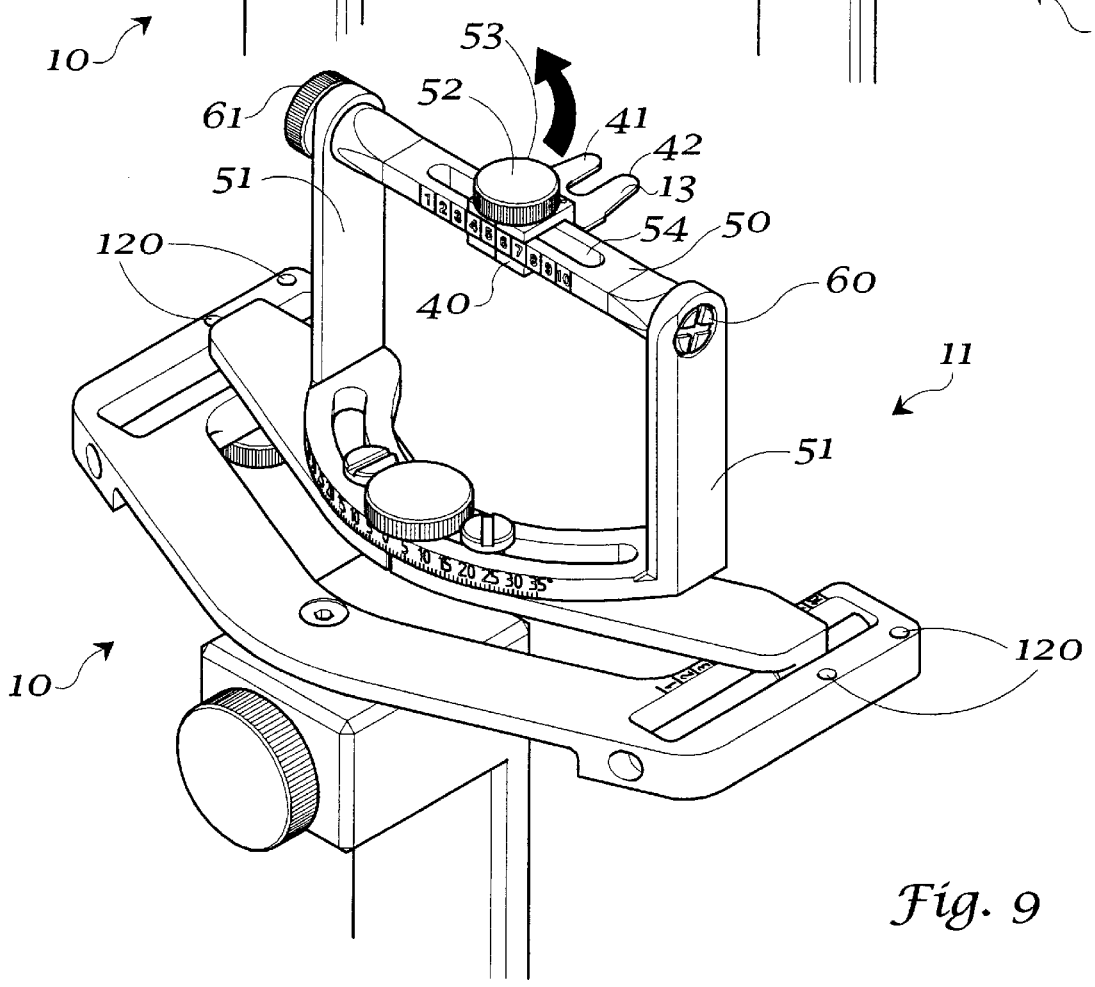

FIG. 9 shows a horizontal position substantially perpendicular to the adjustable position shown in FIG. 11. It would be appreciated, that the positioning shown in FIGS. 8–11, can be achieved for example by vernier adjusting mechanisms, although any adjusting mechanism is within the scope of the invention.

For example, support bar 40 may be adjustably affixed to a support rod 50, which in turn is supported on legs 51. A threaded clamp mechanism 52 is affixed to support 40 such that as support 40 is horizontally positioned along support rod 41, it can be locked into place, such as for example, by turning knob 53. Knob 53 thereby creates a simple compression fitting, which when removed allows freedom of movement of support rod 40 along support rod 41. Preferably, knob 53 is a thumbscrew threadably engageable with bar 40 through a slot 54 in rod 41.

Support rod 41 is also rotatable such as for example, on axle nut 60. Threaded knob or thumbnut 61 is provided on at least one end of support rod 41, and, when tightened, draws support rod 41 into physical contact with a leg 42 (depending upon with which leg It is associated), thereby restricting the freedom of rotation support rod 41 upon axle 61. Thus, the rotational position of support rod 41 can be obtained and removably affixed.

Figure 4:
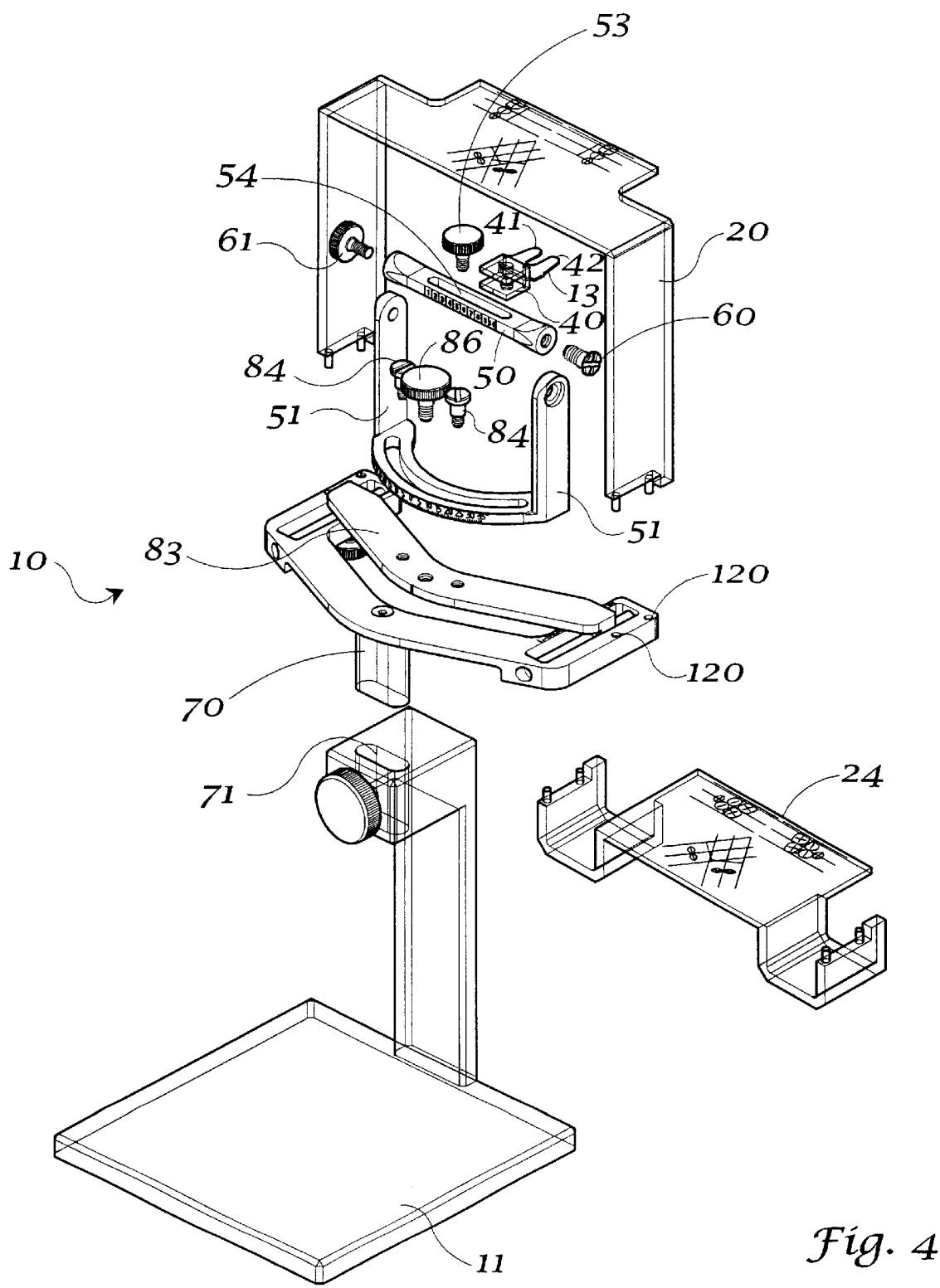
FIG. 4 is a partially exploded, perspective view of the apparatus of FIG. 1.

FIG. 1 also shows a support block 70 which can be used to removably affix positioning apparatus 10 to alternatively and selectively, workbench support 11 and a desired x-ray machine 12a. By providing a slot, such as slot 71 (FIG. 4) positioning apparatus 10 can be placed within workbench support 11 and by providing a similar slot upon an x-ray machine 12a, positioning device 10 can be also positioned upon and in conjunction with the x-ray machine 12a. Another thumbscrew 72 can be provided in support 11 to secure it in position in a conventional manner.

Figure 10A:
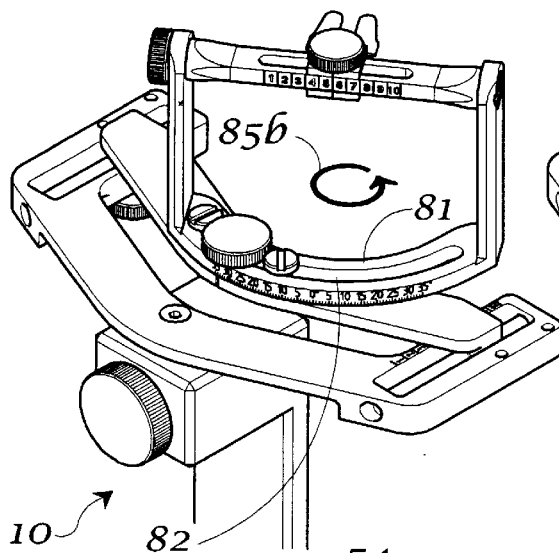
Figure 10B:
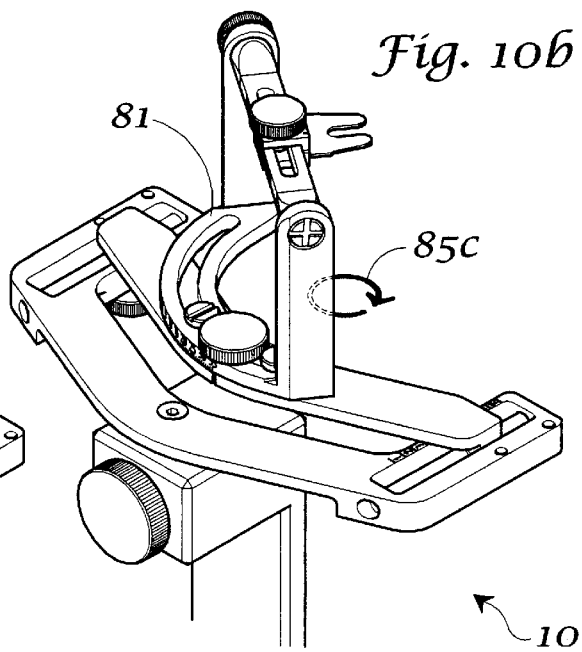
Figure 10:
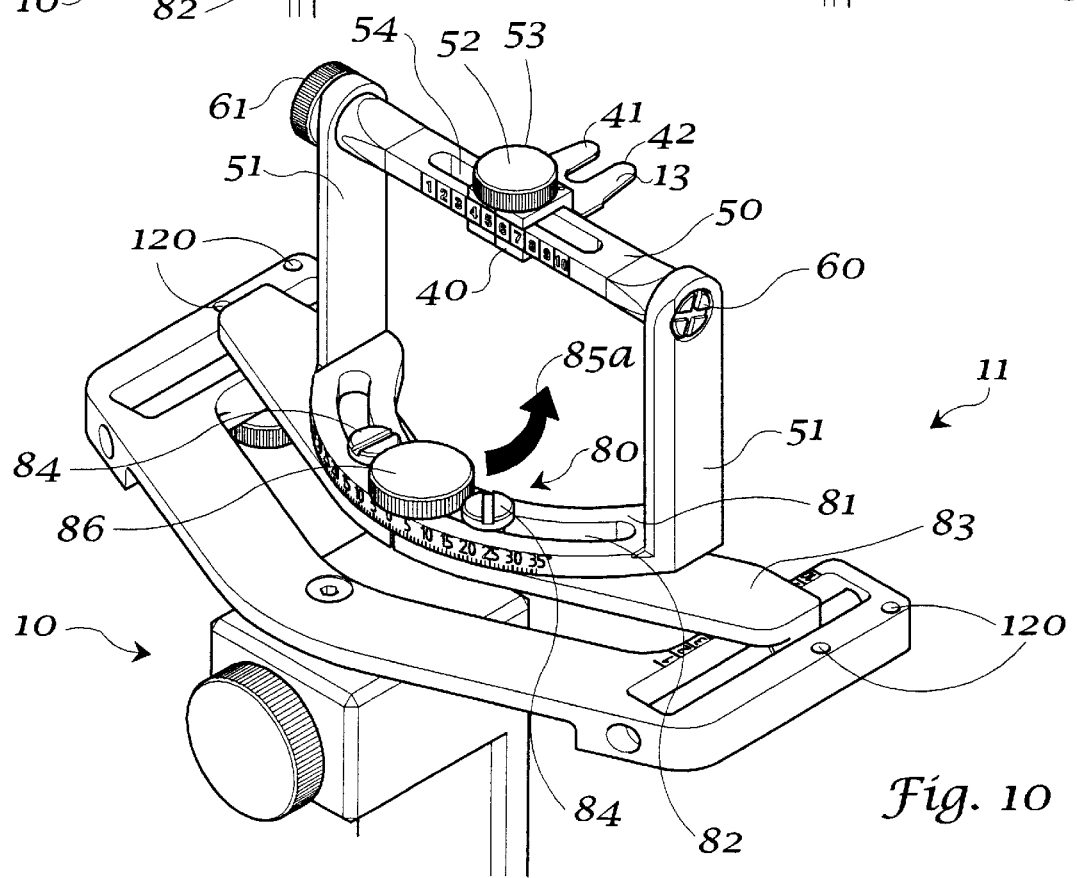

Another vernier adjusting mechanism 80 is shown which can be used to carry out the horizontal adjusting as shown in FIG. 10. FIG. 11 also shows the horizontal adjusting mechanism 90 which can be used to position support bar 40. Base member 81, preferably physically supporting legs 51, may be arcuate in shape, or at least carrying arcuate slot 82. Apparatus 10 also carries sub-base 83, having pins or screws 84, receivable within arcuate slot 82. Thus, base membe 81 can be adjusted in the arcuate manner shown by arrows 85a, 85b and 85c in the drawings (FIG. 10). A thumbscrew 86 may be used to secure base member 81 in any selected location.

As shown in FIG. 11, sub-base 83 may be supported on apparatus 10 by runners 91 received in tracks 92. Horizontal movement is allowable as represented by arrows 93a, 932b and 93c by movement of runners 91 within tracks 92. Thumbscrew 94 may be threadable engaged with sub-base 83 to secure it in a desired location. Indicia 100 may be used on apparatus 10 to help align any of the vernier adjustments discussed hereinabove.

Figure 3:
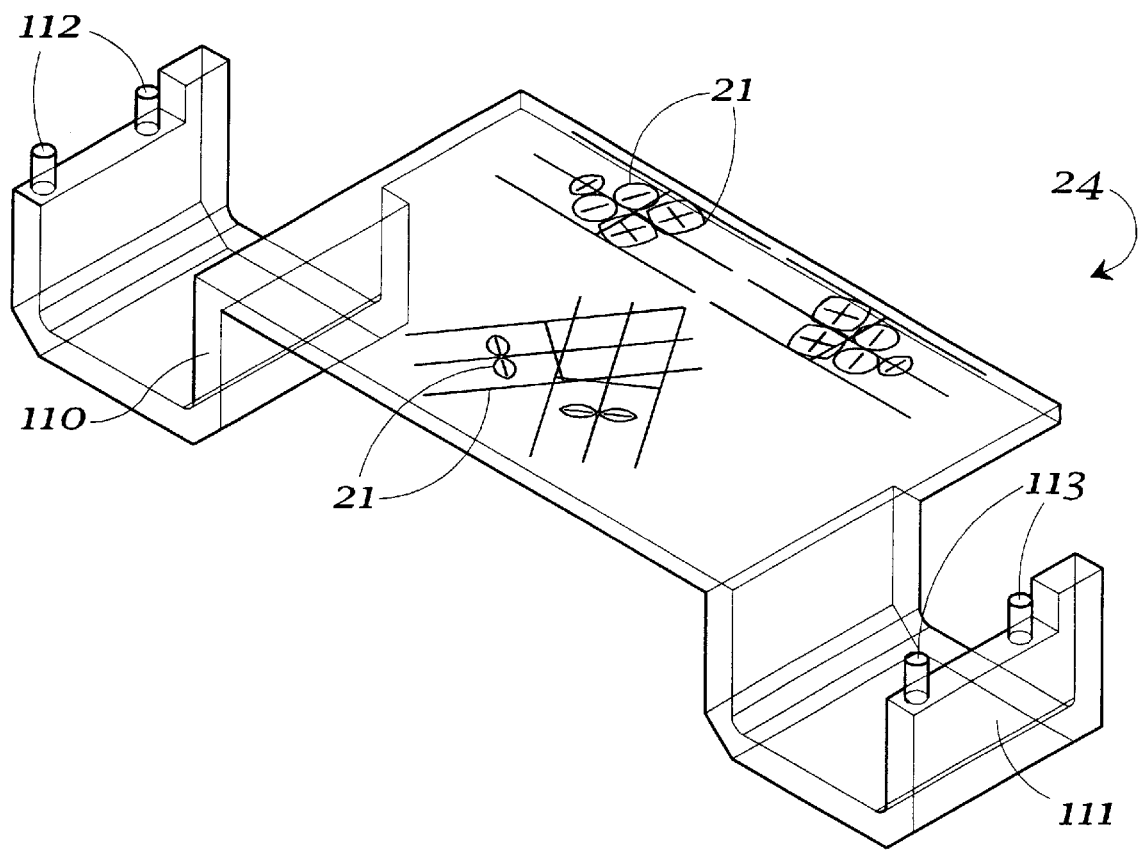
FIG. 3 is a photograph showing a workbench support and a positioning device according to the invention.

FIGS. 2 and 3 shows in guides 20 and 24, showing support legs 110, 111 and pins 112 and 113. It will be appreciated, that pins 112, 113 fit within apertures 120 to position icon guide 20 or 24 upon positioning device 10 as shown in FIG. 1. Any means of removably affixing icon guide 20 or 24 is within the scope of the invention.

It is appreciated that the present invention provides advantages including:

Reproducibility, and comfort of the patient; all critical factors to ensure the success of the examination, which is inherently complex.

The apparatus can be used off-line, with minimised disturbance for the patient.

The positioners offers wide range of adjustments, in the X and Y linear movements, and in the X and Z axis rotation, for the optimal adjustment of the occlusal plane both for upper and lower jaw.

The alignments are simple and accurate, optically guided by gauges and scale indications for optimal reproducibility of the examination.

The device can either use standard trays commercially available, or specifically designed trays.

The trays with the impression can be re-used, which is useful in case of required repetition of the examination at a later time.

The apparatus offers two operation modalities for the positioning of the patient:

The first by using the trays with the impression, where the patient is positioned by biting on the same impression.

The second by using a bite piece, alternative to the tray, and positioning the patient by means of conventional centring lights referred to the alatrago plane (upper jaw) or by placing the mandible in the horizontal plane (lower jaw).

Panoramic x-ray equipment executes the imaging according to the invention by using the linear tomographic technique.

Multiple programs are available for anterior dentition (incisors) left and right, and for posterior dentition left and right.

Multiple views are made of the region of interest, displaced preferably by 7 mm in parallel planes.

The thickness of the tomographic layer is selectable between preferably 3 and 6 mm.

It should therefore be apparent that the positioning device as described herein carries out the object of the invention and otherwise provides an advance and contribution to the art. The invention has been exemplified with respect to drawings and description, without an attempt to provide a depiction or description of every embodiment of the event of device or method. Those skilled in the art will readily understand that various sizes, components and method steps can be employed and still fall within the scope of the present invention.

What we claim is:

1. A device for positioning a patient for the taking of a dental x-ray, comprising:
  a support bar removably affixable to a dental impression tray, means to adjust the position of said support bar in at least one direction in relation to the desired x-ray location, and, an icon guide having at least one icon and removably positionable in a spaced opposing relation to said impression tray when said impression tray is affixed to said support bar, and, wherein said icon guide is at least partially transparent.

2. A device as in claim 1, wherein said means to adjust includes a rotatable support rod affixed to said support bar.

3. A device as in claim 2, wherein said rod is provided with means to adjust the position of said support bar axially along the length of said rod.

4. A device as in claim 3, wherein said means to adjust includes a clamping means.

5. A device as in claim 1, further comprising means to removably mount the device on an x-ray machine.

6. A device as in claim 5, wherein said means to mount includes a block carried by the device and receivable within a slot carried by the x-ray machine.

7. A device as in claim 6, further comprising in combination, a remote support also carrying a slot for selectively receiving said block.

8. A device as in claim 1, wherein said means to adjust includes an arc arcuate shaped slot carried by a base member, such that the arcuate position of said support bar can be adjusted.

9. A device as in claim 8, wherein the device further comprises a pin means receivable within said arcuate slot, and means to removably restrict movement of said arcuate slot in relation to said pin means.

10. A device as in claim 9, wherein said pin means is a threaded screw, and said means to restrict is a thumbscrew.

11. A device as in claim 1, further comprising a sub-base members having at least one track, and wherein said support bar is supported upon at least one leg member, wherein said at least one leg member is in turn supported by a base member having a runner receivable within said track, such that the horizontal movement of said runners within said tracks is permitted, thereby allowing a corresponding movement of said support bar.

12. A device as in claim 11, wherein the position of said runner within said track is securable in a selected location by use of an affixing means.

* * * * *